United States Patent [19]

Hinaga

[11] Patent Number: 5,569,837
[45] Date of Patent: Oct. 29, 1996

[54] DETECTOR APPARATUS OF DESORPTION GAS AND METHOD THEREFORE

[75] Inventor: Yasushi Hinaga, Machida, Japan

[73] Assignee: ESCO LTD, Tokyo, Japan

[21] Appl. No.: 94,116

[22] PCT Filed: Dec. 3, 1991

[86] PCT No.: PCT/JP91/01684

§ 371 Date: Sep. 20, 1994

§ 102(e) Date: Sep. 20, 1994

[51] Int. Cl.[6] .................................................... G01N 1/00
[52] U.S. Cl. ........................... 73/19.01; 422/78; 422/80; 436/155; 73/863.12; 73/863.11
[58] Field of Search ................... 73/19.01, 863.11, 73/863.12; 422/78, 80; 436/155

[56] References Cited

U.S. PATENT DOCUMENTS 3,946,228   3/1976   Biermann ............................... 73/19.01
5,162,233  11/1992   Komori et al. ...................... 73/863.11

FOREIGN PATENT DOCUMENTS 40-36239  12/1965  Japan .
50-30477  10/1975  Japan .
60-15157   5/1985  Japan .
63-62873  12/1988  Japan .

Primary Examiner—Hezron E. Williams
Assistant Examiner—Daniel S. Larkin
Attorney, Agent, or Firm—Cushman, Darby & Cushman

[57] ABSTRACT

An apparatus which mounts a sample in a vacuum chamber, heats the sample, and analyzes the gas generated from the sample. A loading lock mechanism, enables the vacuum chamber to be maintained at a vacuum even when a measurement is not conducted, and even when a sample is introduced/discharged in/from the chamber, thereby minimizing the background noises and increasing detection performance.

15 Claims, 8 Drawing Sheets

DETECTOR APPARATUS OF DESORPTION GAS AND METHOD THEREFORE

1. Field of the Invention

This invention pertains to an apparatus for analyzing semiconductor chips. More particularly, this invention is applicable in a process of heating a sample (a semiconductor chip) of about 10 mm square in a vacuum, measuring the desorption gas degassed from the sample by a mass spectrometer, and modifying the semiconductor manufacturing process for increasing the yield thereof.

2. Description of the Related Art

There is known a technology for assessment and modification of a semiconductor manufacture process by placing a semiconductor chip sample in a vacuum chamber, irradiating infrared beams thereon to heat the chip, directing the gas desorbed from the chip to a mass spectrometer for measurement, and assessing and modifying the manufacturing process of semiconductors based on the result of the measurement. This technology is extremely effective for increasing the yield of the semiconductor manufacture process.

The prior art apparatus for applying this technology is structured so that an appropriate table for mounting a sample is provided within a vacuum chamber and a silica glass window is opened on the shell of the vacuum chamber to introduce infrared beams into the chamber through the window to heat the sample therein. It is necessary to break the vacuum of the chamber every time a sample is introduced or discharged.

The amount of gas desorped from the sample by heating is extremely small because the sample size is very small, i.e. about 10 mm square and about 1 mm thickness or less, and the manufacture process is controlled to be extremely clean. However, when the vacuum in the chamber is broken as stated above, water vapor is absorpbed on the inner wall of the vacuum chamber, the sample stage in the chamber or the like. As those are heated while the sample is being measured, the gas degassed therefrom acts as a background noise to deteriorate the measurement precision.

This invention aims to solve the problem encountered in the prior art by providing an apparatus for minimizing the background noise which hampers the measurement of gas desorped from the heated sample.

SUMMARY OF THE INVENTION

The inventor of this application has repeated assessment of the process for improving the measurement precision.

The first important point gained for this assessment is not to introduce the environmental air into the vacuum chamber as it causes a background noise. The inventor therefore decided to maintain the vacuum within the chamber for quite a long time, which not only includes the time when a sample is being introduced to or discharged from the chamber but also the time when the measurement is not being conducted. For this purpose, a loading lock mechanism is provided in a space of which volume is sufficiently smaller than that of the vacuum chamber and which is separated from the vacuum chamber by means of a gate valve. When a sample is introduced into or discharged from the chamber, the vacuum of the loading lock mechanism alone is broken. As a sample is being conveyed into the vacuum chamber, the space containing the loading lock mechanism (which will be described as a loading lock chamber hereinafter) is evacuated by means of an evacuating line which is different from the line for maintaining the vacuum in the chamber, and the gate valve is opened. The evacuating line for the space containing the loading lock chamber is preferably an entirely different line from the line used for maintaining the vacuum of the gate chamber, but the evacuating pump may be commonly used in part or as a whole for the two lines, so long as the vacuum in the chamber is not affected when the vacuum within the loading lock chamber is broken.

The second critical point is to heat the sample alone. It was discovered that in the prior art, as infrared beams were introduced through a large glass window opened on the shell of the chamber, it unavoidably heated other places than the sample per se, such as the shell surface or a manipulator in the chamber to create the background gas. Therefore, the inventor placed an infrared lamp outside the vacuum chamber and introduced the infrared radiation into the sample stage by means of a glass rod (especially a silica glass rod) which has a cylindrical form of about 10–40 mm diameter and of 150 mm or longer in length.

The third point is not to keep devices which are not directly relevant to the measurement within the vacuum chamber at the time of measurement. More particularly, the inventor structured the apparatus so that a carrier which conveys a sample from the loading lock chamber to the vacuum chamber is withdrawn from the chamber when the measurement is conducted.

The fourth point is to make the vacuum chamber significantly larger than the sample so that if the sample is heated, the shell of the chamber would not become heated, and even if it is heated, the heat would be easily released therefrom. However, it is meaningless to increase the size of the vacuum chamber unlimitedly because desorption gas is diffused and diluted as the volume of the chamber increases. It was found that keeping the sample away from the shell surface of the vacuum chamber was quite effective. The vacuum chamber was made with metal so as to increase heat conduction. The inner surface was polished to reflect the infrared beams as well as to prevent the gas adsorption.

When an inlet port for the sample provided in the loading lock chamber is opened to receive a sample, the gate valve is closed to keep the vacuum in the chamber unbroken. Before the sample is carried into the vacuum chamber, the space in which the loading lock mechanism is housed is evacuated to a vacuum by means of a vacuum pump of another line, and then the valve is opened and the sample is carried into the chamber. As the volume of the space for the loading lock mechanism is sufficiently smaller than that of the vacuum chamber, the time required to make it vacuum is not long. Gas is unlikely to enter the vacuum chamber when the valve is opened.

When the inner diameter of a vacuum chamber is more than five times the diameter of a sample stage and the distance from the sample stage to the ceiling is 50 mm or higher, the inner wall surface of the vacuum chamber would not be heated even when the sample is heated to degas it. Therefore, the background noise or gas is seldom generated from the inner wall surface.

Conversely, the volume of the vacuum chamber can be made as large as mentioned above because it takes only a short time to create a high vacuum as the vacuum in the chamber is not broken when a sample is let into it.

As the vacuum chamber is made with a metal cylinder and metal flanges, and the inner wall surface thereof is polished so that they reflect infrared radiation to enhance the heating effect as well as to prevent adhesion of dust even if dust happens to enter.

As the loading lock mechanism is structured to permit withdrawal of a carrier for mounting a sample thereon and a transfer mechanism for the carrier from the vacuum chamber, gas released from the carrier and the like does not affect measurement.

The loading lock mechanism is made as a pinion and rack mechanism, a sealing mechanism having a double O-ring is provided on the pinion rotation shaft, and the intermediate space between the double O rings is kept as a vacuum by an evacuating means so that even if an operator rotates the shaft of the pinion by means of a knob and the like to move the carrier into the chamber by operating said transfer mechanism, gas does not leak to the space containing the loading lock mechanism.

As an infrared generator is used as a heater and arranged outside the vacuum chamber and the generated infrared beams are introduced into the sample stage by means of a glass rod, the sample stage alone in the chamber is heated and the background noise is rarely produced at the time of analysis.

When the evacuating pump includes a magnetic levitated turbo molecular pump, the pressure inside the device may be raised to ultra-high vacuum of $10^{-10}$ torr (1 torr is equivalent to 1.33 milibar) order, and the mass spectrometry may be conducted quite precisely.

It is preferable to set the inner diameter of a vacuum chamber five times the diameter of a sample stage and the distance from the sample stage to the ceiling at 50 mm or higher.

If the vacuum must be broken for some unavoidable reason, dry nitrogen or dry air is introduced into the location to prevent entering moisture and the like which might cause the background noise, into the location. When an inlet port of the loading lock mechanism is to be opened, dry nitrogen is introduced to the space outside the gate valve. [BRIEF DESCRIPTION OF THE DRAWINGS]

FIGS. 1(*a*) and 1(*b*) show the entire layout of a first embodiment of this invention; FIG. 1(*a*) shows its frontal view and FIG. 1(*b*) a plan view;

FIGS. 3(*a*)–3(*c*) illustrate the loading lock mechanism of the first embodiment: FIG. 3(*a*) shows its outer perspective view, FIG. 3(*b*) its exploded inner view, and FIG. 3(*c*) a sectional view of a seal mechanism;

FIGS. 4(*a*) and 4(*b*) show a sample stage; FIG. 4(*a*) shows its whole view and FIG. 4(*b*) its detailed view;

FIGS. 6(*a*) and 6(*b*) show a manipulator; FIG. 6(*a*) is a plan view and FIG. 6(*b*) is a cross section;

FIGS. 7(*a*)–7(*c*) are graphs illustrating the spectrometry result; and

DETAILED DESCRIPTION OF THE PRESENTLY PREFERRED EMBODIMENTS

This invention will now be described by referring to preferred embodiments shown in attached drawings.

Figure 1A:
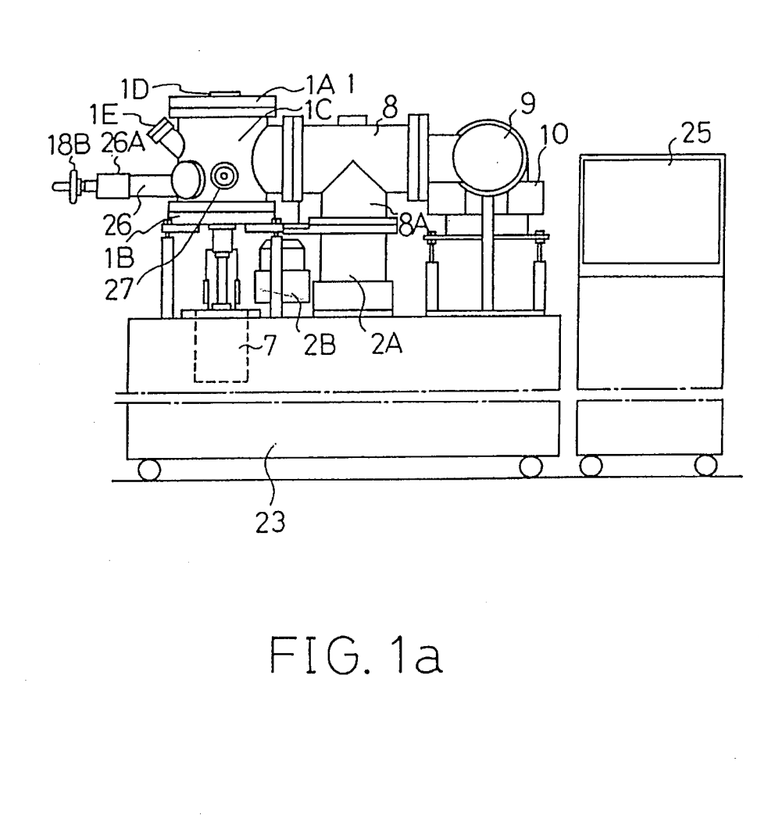
Figure 1B:
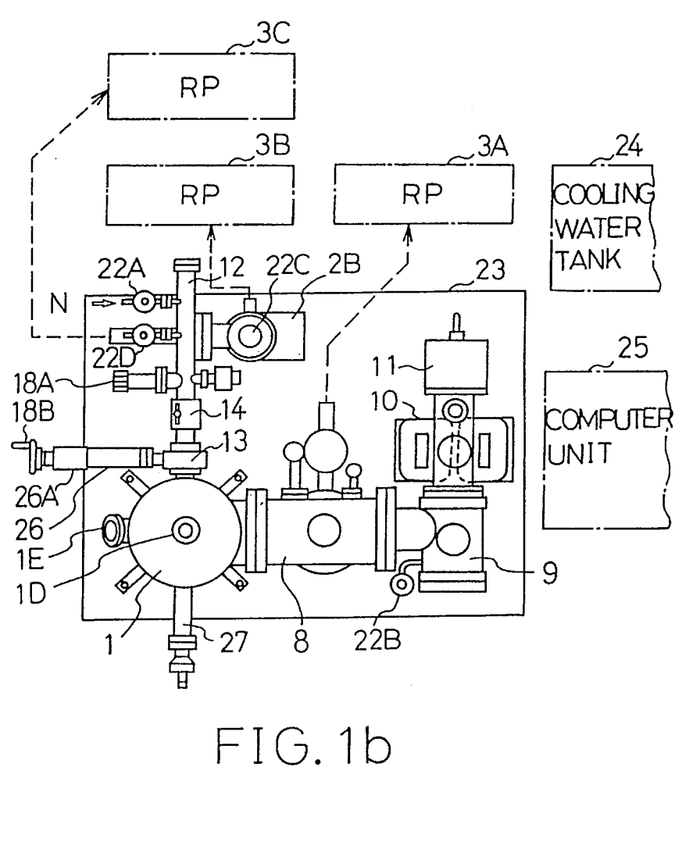
Figure 2:
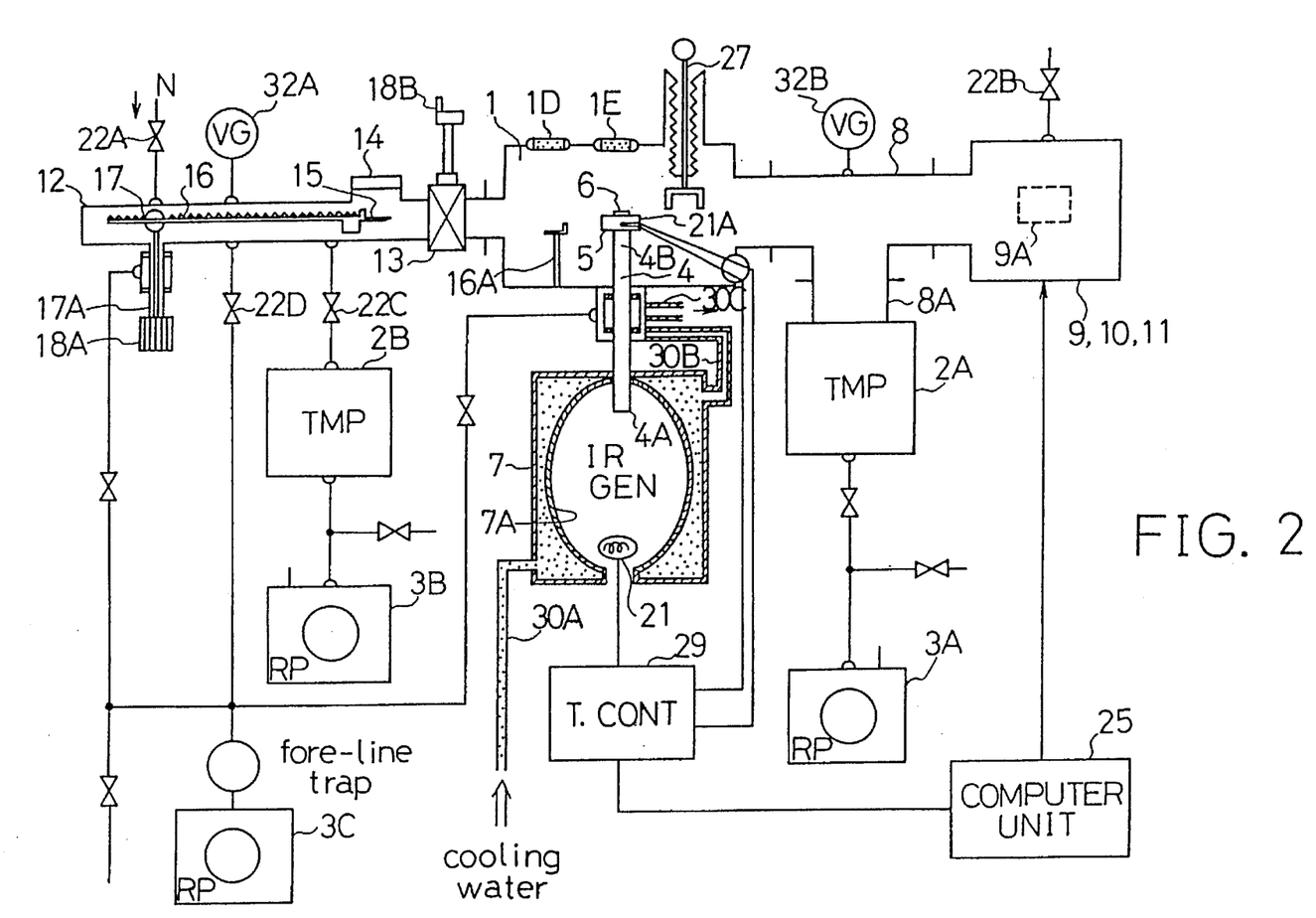
FIG. 2 shows the first arrangement of the embodiment.
Figures 3A, 3B, 3C:
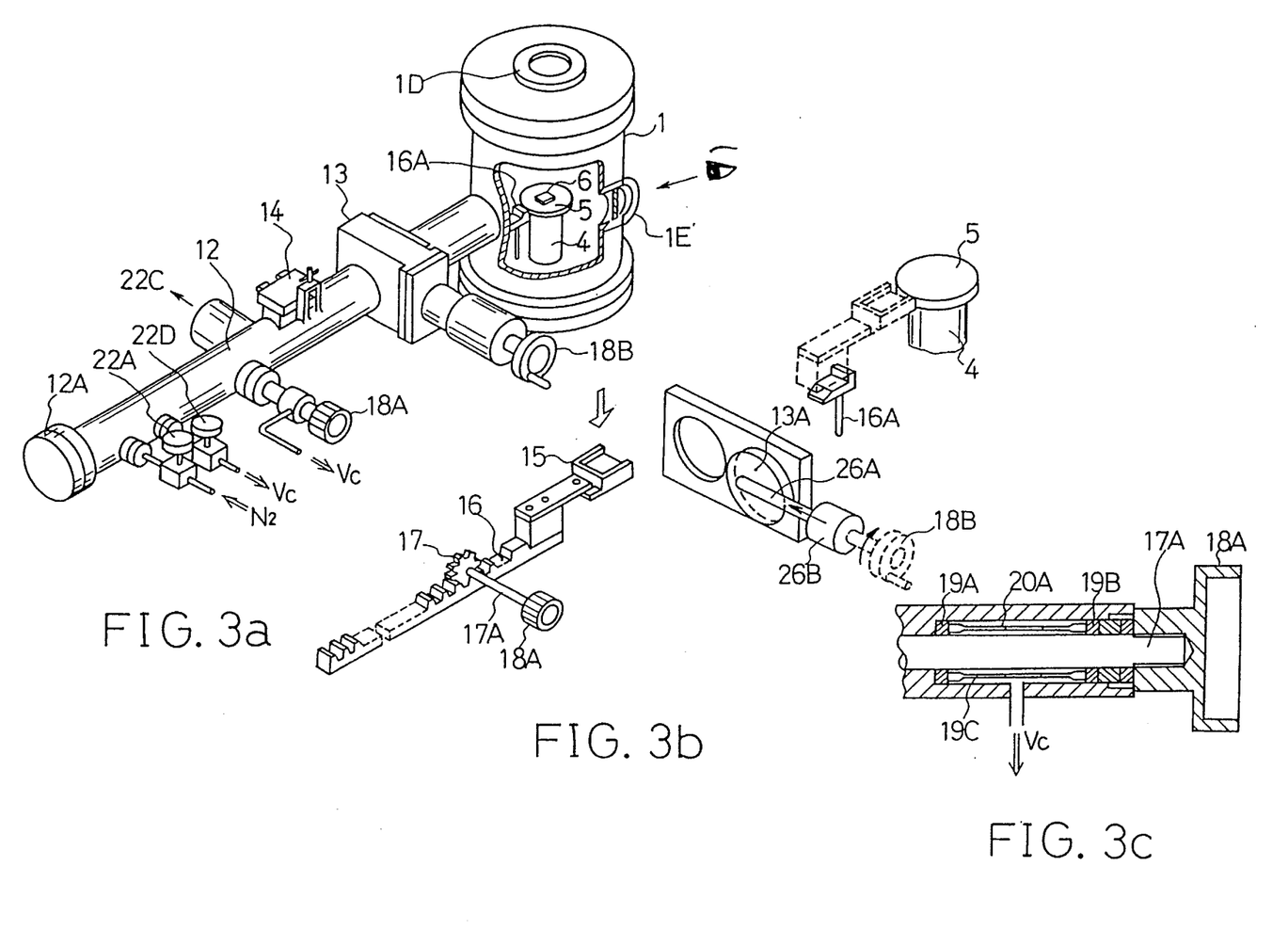

FIGS. 1(*a*) and 1(*b*) show the entire arrangement of an embodiment of this invention, FIG. 2 shows a line system diagram thereof and FIGS. 3(*a*)–3(*b*) are explanatory views for the loading lock mechanism thereof.

In the drawings the apparatus for detecting desorption gas comprises a vacuum chamber 1, vacuum pumps 2A and 3A for keeping the chamber in a vacuum, a sample stage 5 in the chamber 1, a heater 7 for heating a sample 6 which is a semiconductor chip mounted on the upper face of the sample stage 5, and a mass spectrometers (9, 10 and 11) which is connected to the vacuum chamber 1 via a connecting pipe 8.

This invention is characterized as follows:
(1) It is provided with a loading lock mechanism which is covered by a loading lock chamber 12 having a volume sufficiently smaller than the vacuum chamber 1, provided with a gate valve 13 leading to the vacuum chamber 1, which can keep the vacuum in the chamber 12 by means of the vacuum pumps 2B and 3B of a different line from that of the vacuum pumps 2A and 3A so as to transfer a sample which is introduced through an inlet port 14 and to place the sample on the sample stage 5 without breaking the vacuum in the chamber 1.
(2) The vacuum chamber has an inner diameter which is about seven times of the diameter of the sample stage 5, and the distance from the sample stage 5 to the ceiling of the chamber 1 made with metal flanges 1A and 1B is about 200 mm.
(3) The vacuum chamber 1 has a wall structure comprising a metal cylinder 1C and metal flanges 1A and 1B and the inner wall surface thereof is polished.
(4) The loading lock mechanism is structured in a manner to permit withdrawal of a carrier table 15 for mounting a sample temporarily and a rack 16 which transfers the carrier table 15 from the vacuum chamber 1.
(5) The loading lock mechanism includes a pinion 17 which engages with the rack 16. The pinion 17 has a rotating shaft 17A which rotates by means of an outer knob 18A, the pinion shaft 17A is provided with a sealing structure having an intermediate evacuated chamber 20A wherein double O rings 19A and 19B are arranged at predetermined positions separated from each other by a spacer 19C, and a rotary type vacuum pump 3C of a line different from those of vacuum pumps 2A, 3A, 2B and 3B is provided to keep the inside of the intermediate chamber 20A in vacuum.
(6) The heater 7 is an infrared generator 7 having a reflection surface 7A of spheroidal shape with an infrared generator lamp 21 arranged at one focus and a light incident surface 4A of a transparent silica glass rod arranged at another focus. The generator 7 is placed outside the vacuum chamber 1, and sample stage 5 is placed above the glass rod 4 which is suspended in a manner to emit the infrared beams generated by the generator 7 from the other end surface 4B opposing the incident surface 4A.
(7) Of the vacuum pumps, 2A denotes a magnetic levitated turbo molecular pump and 2B a turbo molecular pump so that the inside of the vacuum chamber 1 can be maintained in high vacuum of at least $10^{-9}$ torr, and the inside of the loading lock chamber 12 in high vacuum of at least $10^{-8}$ torr.

The desorption gas detection method according to this invention is characterized as follows.
(1) While the vacuum chamber 1 is kept in high vacuum, a sample can be introduced into or discharged from the sample stage 5 in the chamber 1 through an inlet port 14.
(2) If the vacuum must be broken, dry nitrogen or dry air is introduced therein. More specifically, when the vacuum in the loading lock chamber 12 is to be broken, dry nitrogen or dry air is introduced into the chamber 12 by manipulating a cock 22A while the vacuum in the chamber 1 is broken, dry nitrogen or dry air should be introduced therein by manipulating a cock 22B.

The layout of the apparatus according to this invention will now be described by referring to FIGS. 1(*a*)–1(*b*).

Almost all the component parts of this embodiment are placed on a desk 23 except for rotary pumps 3A, 3B and 3C of the vacuum pumps, a cooling water tank 24, and a computer unit 25 which are placed outside the desk 23.

The gate valve 13 is provided with a shaft 26 which opens/closes a sliding valve 13A (FIG. 3(b)) by rotating a knob 18B at end 26A of shaft 26, and the shaft 26 is sealed with bellows. The vacuum chamber 1 is communicated with an ionization region 9 of a mass spectrometer via a connection pipe 8 having a larger diameter. The pipe 8 is connected to a magnetic levitated turbo molecular pump 2A via a main evacuation pipe 8A. A magnetic field region 10 and a collector region 11 are provided adjacent to the ionization region 9. A manipulator 27 is provided at a position opposing the loading lock mechanism of the vacuum chamber 1. The manipulator 27 functions to transfer a sample from or to a carrier table 15 which approaches the sample stage 5 by said rack 16.

Function of each component part will now be described.

In the loading lock mechanism shown in FIGS. 3(a)–3(c), the carrier table 15 and the rack 16 are placed on the side of the end 12A of the chamber 12 and the carrier table 15 is positioned substantially below the sample inlet port 14. The gate valve 13 is closed by the sliding valve 13A. When the inlet port 14 is to be opened, the cock 22A is opened in advance to fill the chamber 12 with dry nitrogen $N_2$, and then the inlet port 14 is opened and the sample is mounted on the carrier table 15. Then, the cock 22A is closed, the cock 22D is opened to conduct preliminary evacuation, and then the loading lock chamber 12 is evacuated after opening the cock 22C.

After the chamber 12 has fully been evacuated, the gate valve 13 is opened, and the pinion 17 is rotated by means of a knob 18A to move the rack 16 to the side of the chamber 1. As the carrier table 15 approaches a predetermined position on the stage 5, the end of the rack 16 contacts a stopper 16A in the vacuum chamber 1.

Figure 6A:
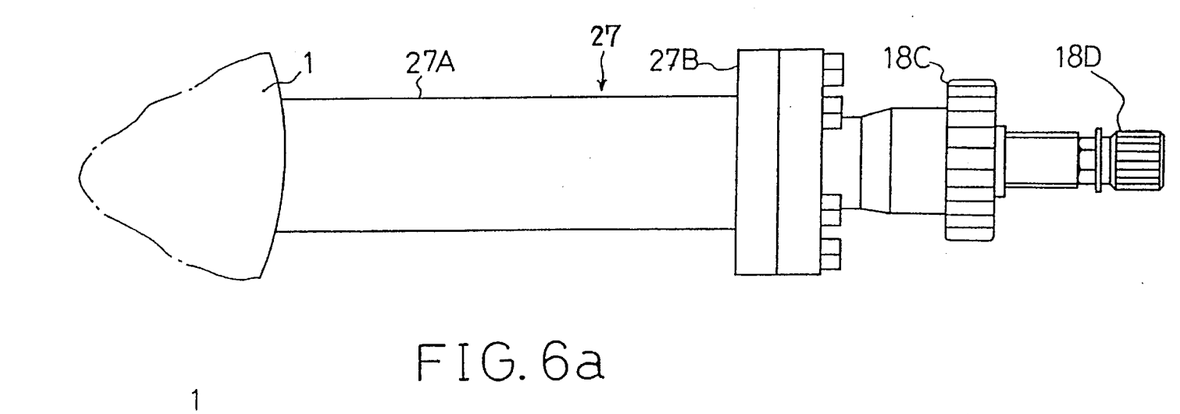
Figure 6B:
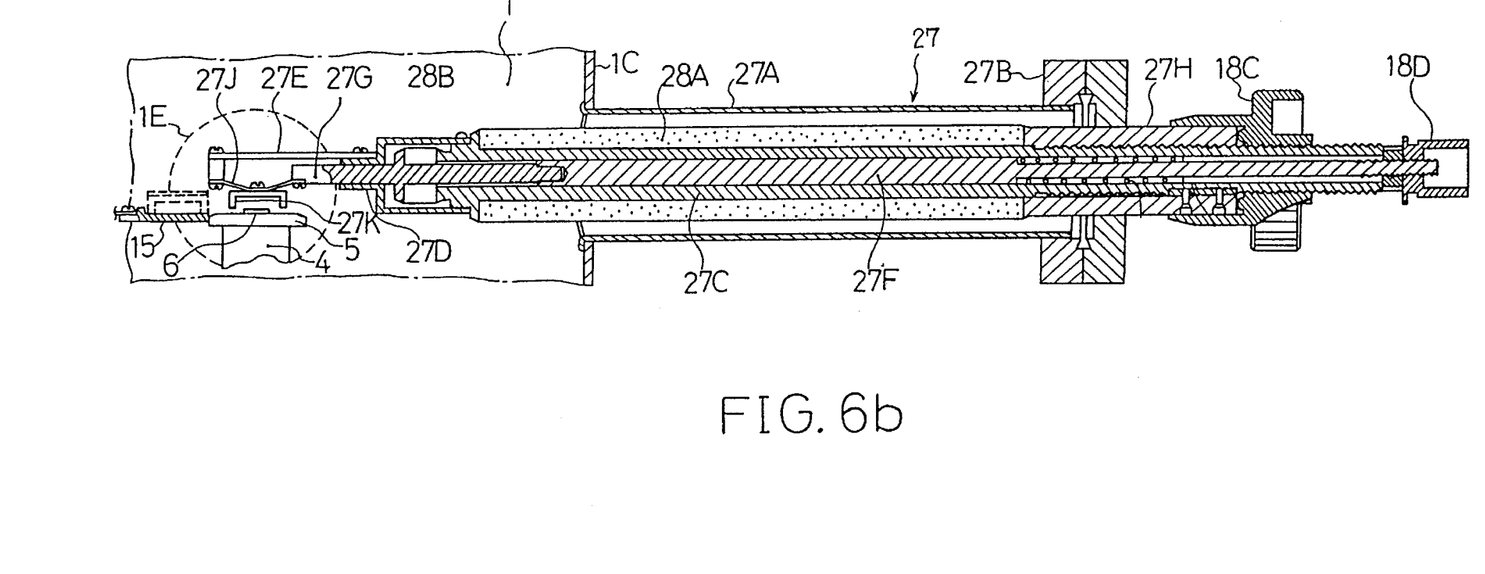

The sample mounted on the carrier table 15 in this state is transferred to the stage 5 by means of a manipulator 27 which is illustrated in FIGS. 6(a)–6(b).

In FIG. 6(b) which shows the manipulator 27 in cross section. The metal cylinder 1C which is the shell of the vacuum chamber, has a sleeve 27A of a rigid structure and a flange 27B. The first and second operation terminals or knobs 18C and 18D are provided outside the flange 27B under the atmospheric pressure.

There is provided a tubular shaft 27C which moves substantially horizontally in a radial direction from the center of the vacuum chamber by manipulation of the first operation terminal or the knob 18C, and a first operation end 27E is provided on one end thereof via a bearing 27D.

An inner shaft 27F is provided inside of the shaft 27C in the longitudinal direction thereof to vary the relative position, and the second operation terminal or the knob 18D is attached at the outer end of the shaft 27F while a second operation end 27G is attached at the other end of the shaft 27F.

A first bellows 28A covers the section between the tip end of the shaft 27C on the inner side of the chamber and a seat 27H fixed on the flange 27B to expand/contract according to the displacement of the shaft 27C while a second bellows 28B covers the section between the shaft 27F and the shaft 27C to expand/contract according to the relative displacement of the outer and inner shafts 27C and 27F. A U-shaped pawl 27K is suspended by a plate spring 27J between the first and second operation ends 27E and 27G.

The leakage to the vacuum chamber which might otherwise be caused when operation terminals are being handled is prevented by providing the two bellows.

Under the normal state, i.e., when a sample is not replaced, the outer and inner shafts 27c and 27F are drawn out in the right side of the figure by manipulation of the knob 18C, and the first bellow 28A is contracted while the first and second operation ends 27E and 27G are drawn in the direction of the sleeve 27A.

As stated above, when the carrier table 15 of the loading lock mechanism approaches the stage 5, the outer and inner shafts 27C and 27F are inserted into the vacuum chamber by the first operation terminal or the knob 18C to move the pawl 27K to the position marked with broken lines. Close to the carrier table 15, the knob 18D should be handled to press the inner shaft 27F to the left side of the figure in respect of the outer shaft 27C. This expands the second bellows 28B and shortens the distance between the first and second operation ends 27E and 27G to push out the plate spring 27J and to lower the pawl 27K. As the outer and inner shafts 27C and 27F are moved toward the right in FIG. 6(b) by manipulating the knob 18C, the sample on the carrier table 15 is transferred to the stage 5. In this way, samples may be transferred.

These manipulations are conducted while observing the sample through viewing windows 1E and 1D (shown with the broken line in FIG. 6(b)) placed on the metal cylinder 1C of the vacuum chamber.

Referring again to FIG. 2, infrared generator 7 is arranged outside and underneath the vacuum chamber 1, and infrared beams generated from the infrared generation lamp 21 arranged at a focus of a reflection surface 7A of spheroidal form inside the generator is absorbed through the light incident surface 4A of a silica glass rod 4 placed at another focus point and is irradiated to the lower surface of the sample stage 5 through the other end surface 4B. The lamp 21 heats the sample stage 5 at a predetermined temperature with electric current transmitted from a temperature controller 29 which is controlled by a computer unit 25. In order not to dissipate the heat of the reflection surface 7A to outside of the generator 7, cooling water is cycled from a cooling water tank 24 (FIG. 1(b)) to the outside of the reflection surface 7A via a pipe 30A.

Figures 4A, 4B:
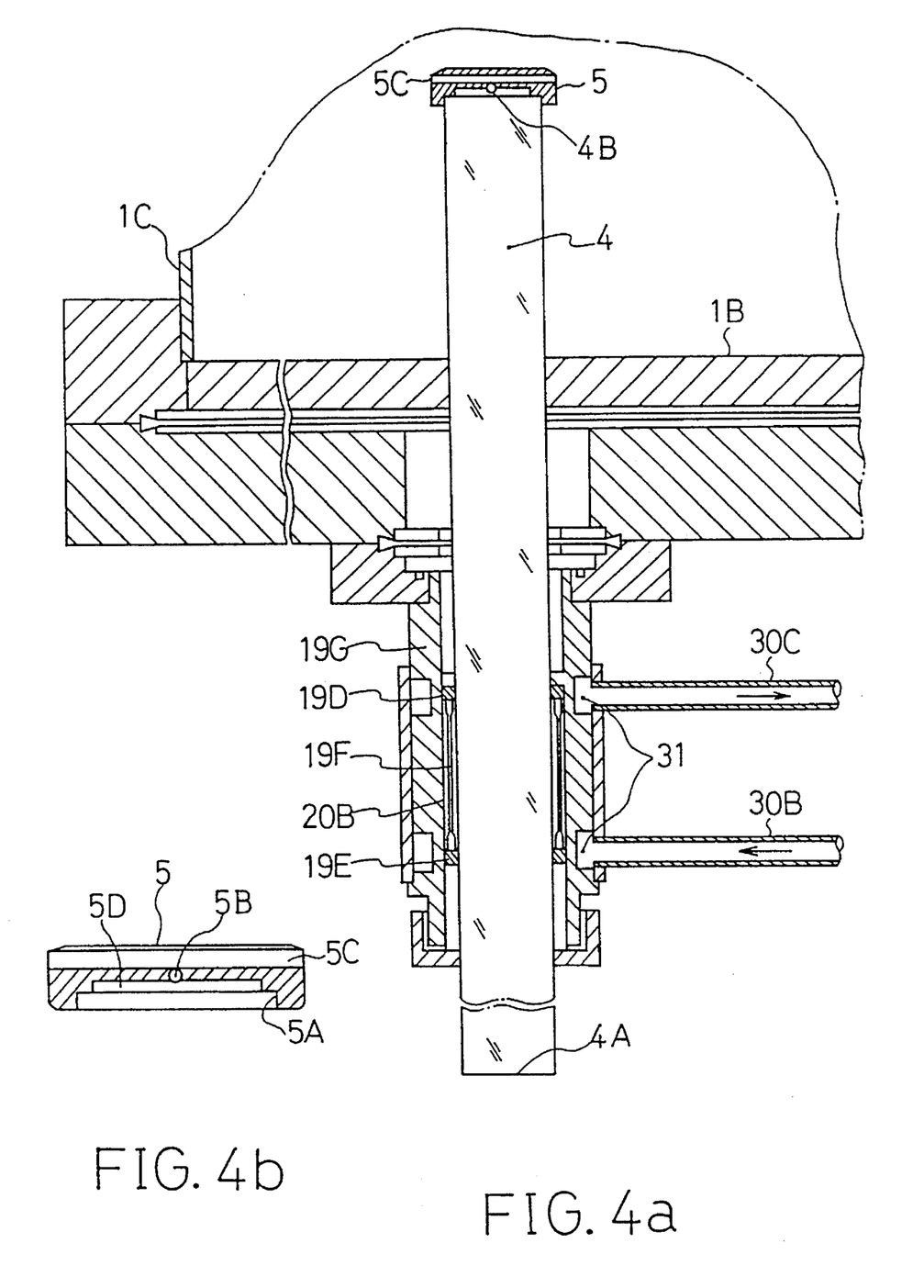

FIG. 4(a) shows the sample stage wherein the glass rod 4 is made of transparent silica glass and the stage 5 is made of opaline silica glass. As shown in FIG. 4(b), which is a detailed view of sample stage 5, the sample stage 5 is loosely engaged at a hollow 5A with the surface 4B of the glass rod 4. A hole 5B is provided in stage 5 connecting gap 5D and the atmosphere in the vacuum chamber. Therefore, even if the sample stage 5 is heated, the glass rod 4 would not be heated. The hole 5C above the sample stage 5 is provided to receive a thermocouple 21A (see FIG. 2).

Another sealing structure is provided at a portion where the glass rod 4 penetrates through a metal flange 1B of the vacuum chamber. Similar to the one provided on the pinion shaft 17A of the loading lock mechanism mentioned above, the sealing structure includes double O rings 19D and 19E and a spacer 19F which are provided in an intermediate evacuated chamber 20B to maintain the vacuum inside the chamber 1. The intermediate chamber 20B is evacuated by a vacuum pump 3C, which is an evacuating means having a line that is different from the vacuum pumps for the vacuum chamber 1 or loading lock chamber 12.

Having cooled the infrared generator 7, the cooling water is circulated via a pipe 30B to a cooling water passage 31 provided outside of the intermediate chamber 20B and to the tank 24 via the pipe 30C. The sealed portion is cooled with the water and is free of troubles which might otherwise be caused to hamper the maintenance of the vacuum state.

Figure 5:
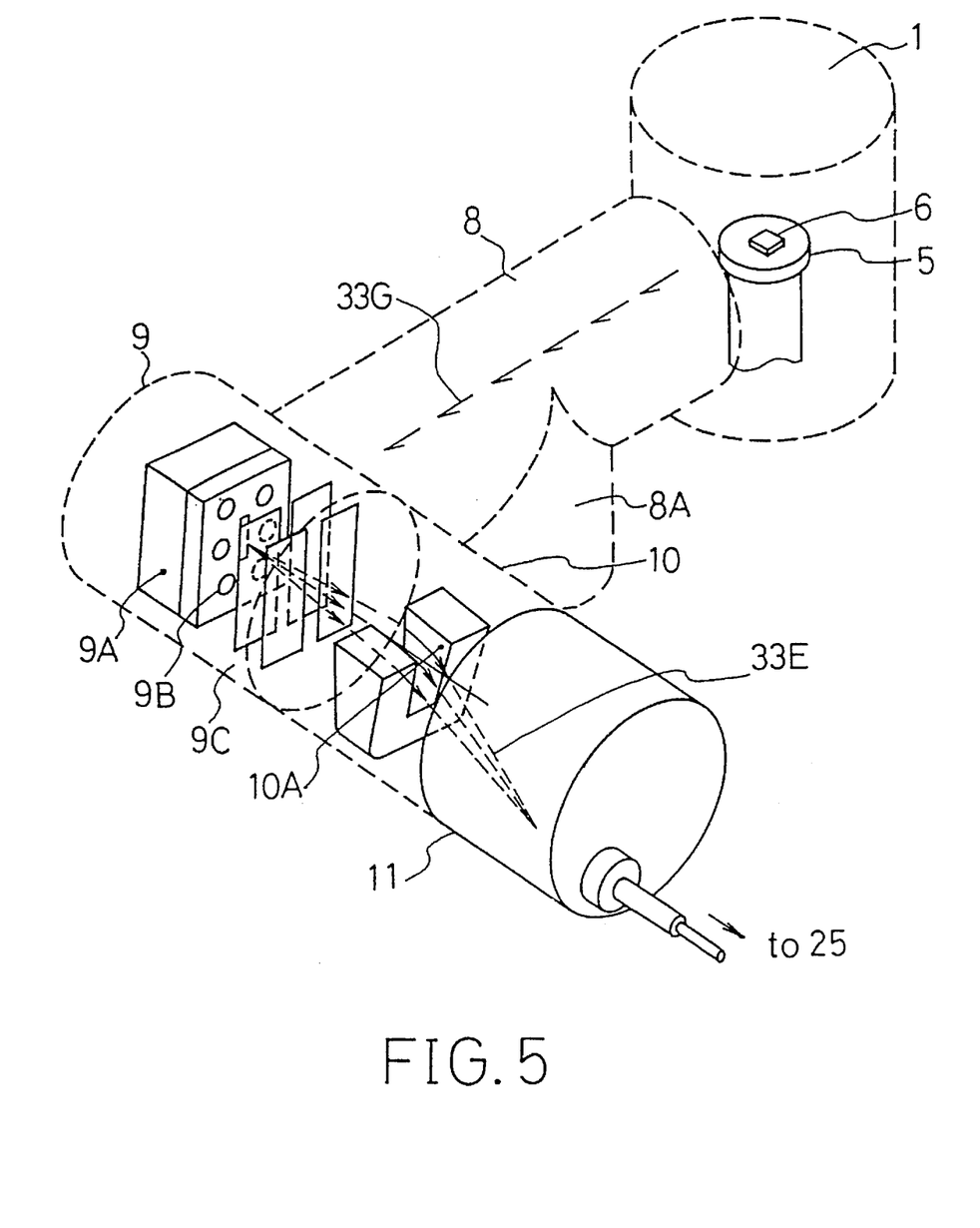
FIG. 5 shows the structure of a mass spectrometer.

FIG. 5 shows a mass spectrometer in the structure.

As shown in the figure, an ionization chamber 9A inside the ionization region 9 is of an open type having plural openings 9B, and the ionization region 9 is communicated with a short thick connecting pipe 8.

According to the usual method of introduction of a sample into a mass spectrometer, the desorption gas generated from a sample 6 on the sample stage is accumulated temporarily and directed to an ionization chamber 9A through a narrow passage. There is a certain time lag from the time point the desorption gas is generated and the time point the gas is ionized by electrodes, making analysis in real time impossible.

According to this invention, the desorption gas 33 generated from the sample 6 is directed immediately into the ionization chamber 9 without being accumulated through the opening 9B into the chamber 9A, and is ionized by the impact of the electron beams from the filaments (not shown). Ion beams 33E, which are withdrawn from the ionization chamber 9A by an electrode 9C, are deflected by the magnetic field of the magnetic pole 10A of the region 10 and detected by a collector region 11.

Referring now to FIG. 2, the operation of the embodiment will now be described.

*The gate valve 13 is closed, the cock 22A is opened, and dry nitrogen $N_2$ is filled in the loading lock chamber 12.
 *The sample inlet port 14 is opened, and a sample is placed on a carrier table 15.
 *The cock 22A is closed, and the inlet port 14 is closed.
 *The cock 22D is opened, to evacuate chamber 12 preliminarily by a rotary type vacuum pump 3C.
 *The cock 22D is closed, and the cock 22C is opened to evacuate the loading lock chamber 12 by the turbo molecular pump 2B.
 *The ultimate vacuum attained in the loading lock chamber 12 is confirmed by the vacuum gage 32A, and the valve 13 is opened.
 *The pinion 17 is rotated by the knob 18A, the carrier table 15 is moved by the rack 16 until it contacts the stopper 16A in the vacuum chamber 1, and the carrier table 15 is moved to the sample stage 5.
 *The sample 6 is transferred from the carrier table 15 to the sample stage 5 by the manipulator 27.
 *The manipulator 27 is moved away from the sample stage 5.
 *The carrier table 15 is withdrawn into the loading lock chamber 12.
 *The gate valve 13 is closed.
 *The ultimate vacuum attained in the vacuum chamber 1 is confirmed by a vacuum gage 32B.
 *A temperature rise program is loaded to control the temperature controller 29 by a computer unit 25.
 *The mass number for the desorption gas to be measured by the mass spectrometer is set by the computer unit 25.
 *Analysis is started (temperature is raised, the signal for the temperature is taken in by the computer unit, and at the same time the ion current signal of the mass number set in advance is taken in.)
 *The analysis and measurement are completed.
 *The gate valve 13 is opened, the carrier table 15 is moved to the side of the stage 5, and the sample is transferred to the carrier table 15 by means of the manipulator 27.
 *The carrier table 15 is withdrawn to the inside of the loading lack chamber 12, and the gate valve 13 is closed.
 *The cock 22A is opened, and the loading lock chamber 12 is filled with dry nitrogen $N_2$.
 *The inlet port 14 is opened to replace the sample with a new one.
 *Meanwhile, the computer unit 25 processes the analysis data and outputs a result by printing the pyrogram showing the relation of ionic current against temperature.

Figure 7A:
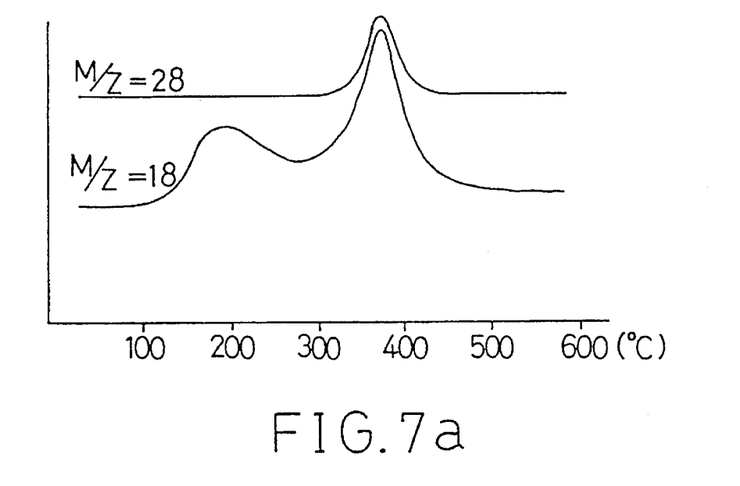
Figure 7B:
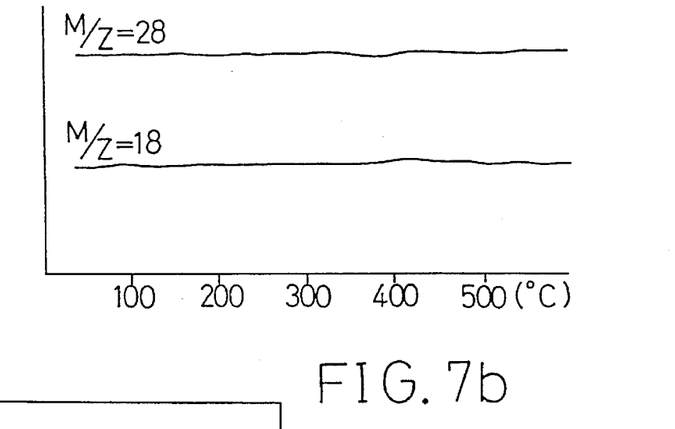

FIGS. 7(a) and 7(b) show the pyrogram of the result of the analysis conducted by this apparatus. In the graph, the vertical axis plots the relative values of the ion current. As shown in FIG. 7(a), the ion current value stays substantially constant before and after the peak value both for the mass number M/z=18 ($H_2O$) and the mass number M/z=28 ($C_2H_4$). In other words, this means the mixed noise is extremely small. FIG. 7(b) shows the measurement values when a sample is not inserted showing that the values for M/z=18 and M/z=28 do not change. This means that there is no background noise which might otherwise be caused by desorption gas from places other than the sample.

Figure 7C:
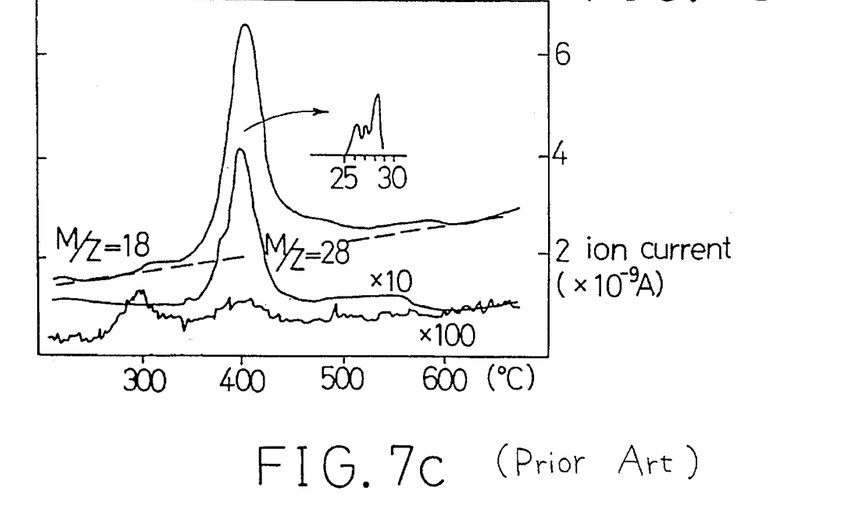
Figure 8:
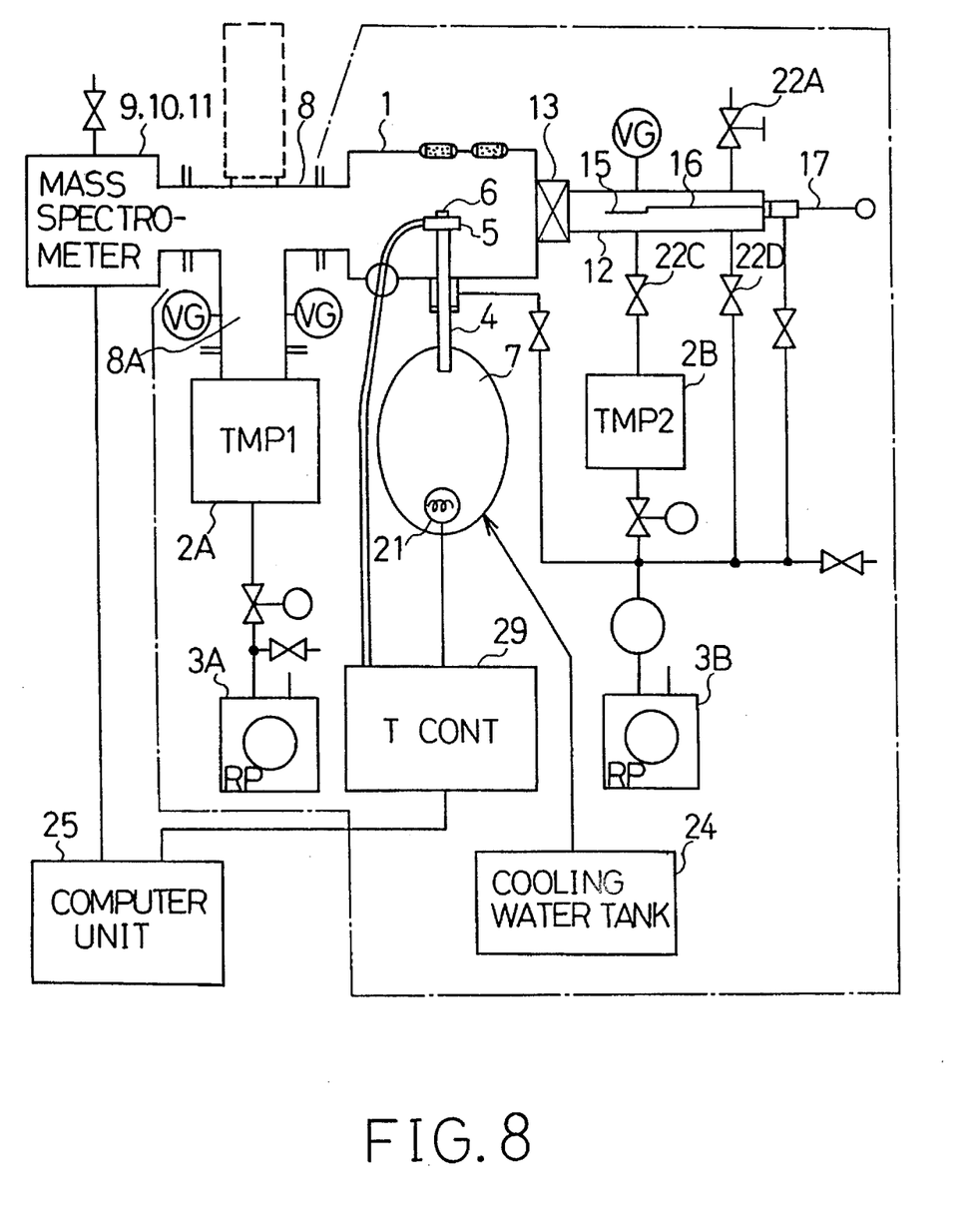
FIG. 8 shows another embodiment in a system diagram.

As a comparative example, FIG. 7(c) shows an example of the measurement analysis which was reported as the best of the recent examples at the meeting of the Institute of Electrical & Electronic Engineers (IEEE) in April, 1990. In the graph, the vertical axis plots the absolute values of the ion current processed. In the case of the curve of M/z=18, for example, the flat portion after the peak value on the side of the high temperature is higher than the flat portion before the peak on the side of the lower temperature as indicated by broken lines. This may be attributable to the effect from the background noise. FIG. 8 shows a system diagram of another embodiment of this invention. As this is similar to the first embodiment shown above except for the pipe lines and valves, the detailed explanation is omitted.

INDUSTRIAL APPLICABILITY

As stated in the foregoing statement, according to this invention, generation of the background gas is extremely small at the time of detection of the desorption gas of a sample by mass spectrometry. This invention method permits precise measurements in real time. This invention enabled precise detection of defects at each manufacture step of samples such as a semiconductor chip. This invention is therefore quite effective to minimize the percentage of defects in manufacture steps of semiconductors and to greatly increase the yield.

What we claim is:

1. A desorption gas detection apparatus comprising:

a vacuum chamber;

a vacuum pump that maintains a vacuum in said vacuum chamber, said vacuum pump being connected to said vacuum chamber by a first line;

a sample stage located at a fixed position inside said vacuum chamber;

a heater for heating a sample placed on said sample stage while not substantially heating components defining said vacuum chamber;

a mass spectrometer connected to said vacuum chamber;

a loading lock mechanism housed in a space having a volume that is smaller than that of said vacuum chamber, said loading lock mechanism including a gate valve connecting said space to said vacuum chamber; and an evacuating means connected to said space via a second line different from said first line to maintain a vacuum in said space, wherein said loading lock mechanism transports and mounts a sample on said sample stage without breaking said vacuum in said vacuum chamber.

2. The desorption gas detection apparatus as claimed in claim 1, wherein heating said sample while not substantially heating said components of said vacuum chamber is achieved by defining an inner diameter of said vacuum chamber said inner diameter is at least five times greater than a diameter of said sample stage, and wherein a distance between said sample stage and an inner wall surface of said vacuum chamber is at least 50 mm.

3. The desorption gas detection apparatus as claimed in claim 1, wherein heating said sample while not substantially heating said components of said vacuum chamber is achieved by providing said vacuum chamber with a shell structure comprising a metal cylinder and metal flanges, and wherein inner surfaces of said metal cylinder and said metal flanges are polished.

4. The desorption gas detection apparatus as claimed in claim 1, wherein said loading lock mechanism comprises a carrier for transporting said sample into said vacuum chamber, a transfer mechanism for mounting said sample on said sample stage and a structure which allows said carrier and said transfer mechanism to be withdrawn from said vacuum chamber.

5. The desorption gas detection apparatus as claimed in claim 1, wherein said loading lock mechanism includes a pinion and a rack mechanism, and wherein a sealing structure with double O rings is provided on said rotary shaft of said pinion, and said loading lock mechanism further includes an evacuating means which maintains a vacuum in a space formed between said double O rings.

6. The desorption gas detection apparatus as claimed in claim 1, further comprising a manipulator that moves said sample from said loading lock mechanism to said sample stage.

7. The desorption gas detection apparatus as claimed in claim 1, wherein heating of said sample while not substantially heating said chamber is achieved by using an infrared generator which is arranged outside said vacuum chamber as said heater, and said sample stage is disposed on one end of a glass rod, another end of said glass rod receiving infrared radiation generated from said infrared generator so that said glass end provides said infrared radiation to said sample located on said sample stage.

8. The desorption gas detection apparatus as claimed in claim 7, wherein said gas rod comprises transparent silica glass.

9. The desorption gas detection apparatus as claimed in claim 7, wherein said heater further comprises an ellipsoid mirror, said infrared generator being provided at a first focus point of said ellipsoid mirror and an end of said glass rod being provided at a second focus point of said ellipsoid mirror.

10. The desorption gas detection apparatus as claimed in claim 9, further comprising a water cooling system for cooling said ellipsoid mirror.

11. The desorption gas detection apparatus as claimed in claim 7, within said sample state of disposed on said end of said glass rod such that a gap is defined between an end surface of said glass rod on which said sample stage is disposed and said sample stage.

12. The desorption gas detection apparatus as claimed in claim 1, wherein said vacuum pump includes a magnetic levitated turbo molecular pump.

13. The desorption gas detection apparatus as claimed in claim 1, wherein heating said sample while not substantially heating said components of said vacuum chamber is achieved by providing said vacuum chamber such that said vacuum chamber has an inner diameter which is more than five times and less than 20 times a diameter of said sample stage, and wherein a distance from said sample stage and a wall of said vacuum chamber is more than about 50 mm and less than 500 mm.

14. A method of detecting desorption gas which comprises the steps of:

obtaining a vacuum in a vacuum chamber;

introducing a sample into said vacuum chamber without breaking said vacuum;

placing said sample on a stage fixed in said vacuum chamber;

heating only said sample in said vacuum chamber and not substantially heating components defining said vacuum chamber; and measuring desorption gas generated from said sample using a mass spectrometer.

15. The method as claimed in claim 14, wherein one of dry nitrogen and dry air is introduced at a location where said sample is held prior to being introduced to said vacuum chamber when said vacuum is to be broken.

* * * * *